United States Patent [19]

Williams

[11] Patent Number: 4,954,081
[45] Date of Patent: Sep. 4, 1990

[54] DENTAL DOWEL PIN REMOVAL METHOD AND APPARATUS

[76] Inventor: Barkley B. Williams, 316 Concord Woods Dr., Smyrna, Ga. 30080

[21] Appl. No.: 279,027

[22] Filed: Dec. 2, 1988

[51] Int. Cl.$^5$ .............................................. A61C 19/00
[52] U.S. Cl. .......................................... 433/53; 433/74
[58] Field of Search ...................... 433/74, 65, 53, 49, 433/34, 213, 215

[56] References Cited

U.S. PATENT DOCUMENTS

| | | | |
|---|---|---|---|
| 1,670,311 | 5/1928 | Masante | 433/60 |
| 2,754,589 | 7/1956 | Highkin | 332/32 |
| 3,650,032 | 3/1972 | Kestler | 433/53 |
| 4,412,822 | 11/1983 | Blechner | 433/60 |

FOREIGN PATENT DOCUMENTS 8807353 10/1988 PCT Int'l Appl. ................. 433/213

Primary Examiner—Cary E. Stone
Attorney, Agent, or Firm—Thomas & Kerr

[57] ABSTRACT

An apparatus for simultaneously separating segments of a dental cast from a plaster base wherein the segments are mounted to the base with pins positioned within holes that extend through the base with the apparatus comprising a platform and a clamp for positioning the base in a predetermined position spaced from the platform. A set of engaging pins are positionable upon the platform in alignment for insertion into the holes of the base. A threaded driver is provided for moving the platform and engaging pins thereon toward a base located at the predetermined position to engage the engaging pins with the dental cast pins thereby dislodging the pins and separating the segments from the base.

13 Claims, 3 Drawing Sheets

4,954,081

DENTAL DOWEL PIN REMOVAL METHOD AND APPARATUS

TECHNICAL FIELD

The present invention relates to dentistry and particularly to fabrication by dental technicians of dental bridges, splints and the like.

BACKGROUND OF THE INVENTION

In fabricating a dental bridge, it is common for a dentist to prepare teeth that are to receive the bridge by grinding the teeth to a generally upwardly tapered shape. A impression of the prepared teeth is then made by the dentist and typically sent to a dental technician for fabrication of a bridge to fit the prepared teeth. The technician usually fills the impression with gypsum to form a plaster cast of the patient's teeth and a set of parallel tapered metal dowel pins is then secured in the bottom of the cast with a pin underlying each prepared tooth. The cast is then mounted atop a wet plaster base with the parallel pins extending through the base. When the base dries, the bottom of the base is buffed or sanded so that the pin ends are flush with the base bottom. The cast is then cut into segments called working dies with a small saw with each segment or die bearing a cast of a prepared tooth. The working dies can thus be individually removed from the base by pressing their corresponding dowel pins upwardly from the bottom of the base. The segmented cast mounted to the base is then usually covered with wax to form a pattern wax coping pattern of the teeth. When this wax pattern dries, the segmented waxed cast can be separated from the base by pressing the tapered dowel pins upwardly from the bottom of the base whereupon the individual working dies can be removed from the wax with the resulting wax pattern being used to cast the bridge or crown.

Heretofore, the tapered dowel pins have been pressed from the base by hand to separate the waxed cast from the base. Many times, the pins are not dislodged from the holes in the base simultaneously causing some of the working dies to separate from the base before others and consequently resulting in distortion or warping of the wax pattern. A bridge cast from such a distorted pattern also bears the distortion such that it might not fit the patient's teeth. In this event, a new bridge often must be fabricated from scratch. Since it is difficult to determine that a pattern has been warped until the finished bridge is completed, many hours of tedious work molding the bridge from the warped impression is sometimes sacrificed.

A long felt and unaddressed need exists, therefore, for a method and apparatus for simultaneously separating the waxed dies of a dental cast from their plaster base such that the resulting wax pattern does not become warped or distorted. It is to the provision of such a method and apparatus that the present invention is primarily directed.

SUMMARY OF THE INVENTION

Briefly described, the present invention is a method and apparatus for simultaneously separating, the segmented working dies of a dental model cast from their plaster base wherein the working dies have tapered dowel pins that extend through the base to hold the cast in place. The apparatus comprises a platform and means for mounting a dental base in a predetermined position spaced from the platform with the base bottom parallel to the platform. The platform is movable toward a base mounted at the predetermined position and a set of engaging pins are adapted to be placed upon the platform and aligned for insertion into the holes of the base. The engaging pins are of equal length such that upon movement of the platform toward the base, they engage the ends of the dowel dental cast pins simultaneously whereupon further movement of the platform toward the base dislodges the dowel pins and urges the working dies upwardly to separate them from the base. In this way, individual dies of a waxed dental cast are separated from the base simultaneously such that the resulting wax pattern is not warped or deformed. When the waxed cast has been separated from the base, the individual dies can be removed from the wax in the conventional way and an accurately formed dental bridge formed from the resulting wax pattern.

Thus, a method and apparatus is now provided for simultaneously separating waxed segments or dies of a dental cast from their base such that an accurate wax pattern for casting a dental bridge results. Additional features, objects and advantages of the invention will become apparent upon reading the following detailed description in conjunction with the accompanying drawings.

DETAILED DESCRIPTION

Figure 1:
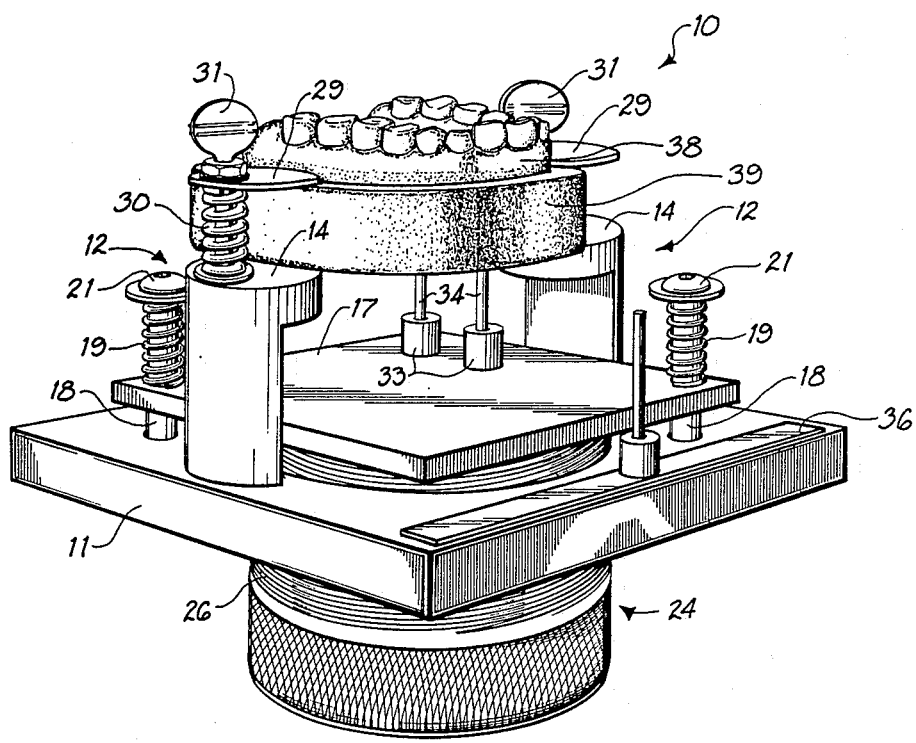
FIG. 1 is a perspective view of an apparatus that embodies principles of the present invention in a preferred form.
Figure 2:
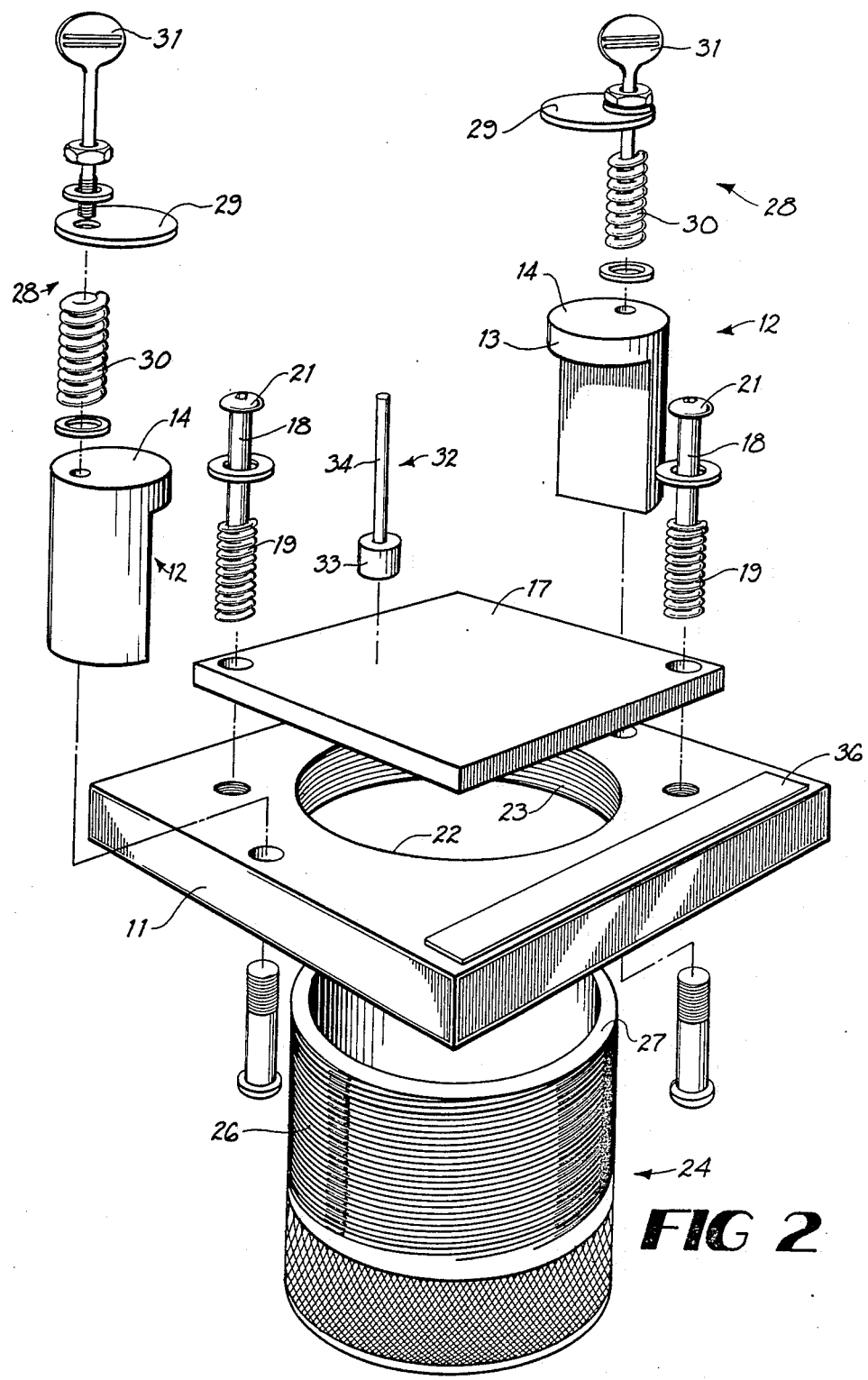
FIG. 2 is an exploded view of the apparatus of FIG. 1 showing placement and relationships of component parts thereof.

Referring now in more detail to the drawings in which like numerals represent like parts throughout the several views, FIG. 1 shows an apparatus 10 for removing dental cast segments or dies from their plaster base wherein the dies have dowel pins adapted to fit into holes that extend through the base. The apparatus 10 comprises a rectangular frame 11 having a pair of support pedestals 12 extending upwardly from opposed edge portions thereof. A rectangular platform 17 is positioned between the pedestals 12 and is movably mounted to the frame 11 by a pair of mounting pins 18 that extend through holes in opposed corners of the platform and are secured to the frame 11 as best seen in FIG. 2. The mounting pins 18 have heads 21 and a coil spring 19 is captured and compressed between the head of each mounting pin 18 and the platform 17. The platform 17 is thereby spring biased toward the frame 11 and can be moved against the force of the coil springs 19 away from the frame 11 with the mounting pins 18 slidably moving through the holes in the platform 17.

As seen in FIG. 2, the frame 11 has a circular opening 22 formed therein with the opening being normally positioned beneath the platform 17 and bearing interior threads 23. A cylindrical driver 24 has a diameter corresponding to the diameter of the opening 22 and bears exterior threads 26 adapted to operatively engage the interior threads of the opening to be advanced into and through the opening upon rotation of the driver. The upper edge 27 of the driver 24 is adapted to engage the lower surface of the platform 17 to support the platform and urge it away from the frame 11 as the driver 24 is advanced through the opening 22. Preferably, the upper edge 27 of the driver 24 is formed to lie always in a plane parallel to the frame 11 such that the platform is supported atop the driver 24 in paced parallel relationship relative to the frame as the platform and frame move apart.

The pedestals 12 have cylindrical upper portions 13 that partially overlie opposed edges of the platform 17 and define flat upper surfaces 14 upon which opposed edges of a dental base can be positioned. The upper surfaces 14 preferably lie in a plane that is parallel to the platform 17 such that the bottom of a dental model base positioned on the pedestals is supported in the plane in spaced parallel relationship relative to the platform 17 as illustrated in FIG. 1. A clamp 28 having a clamping element 29 secured to the pedestal with a thumbscrew 31 and biased upwardly by a coil spring 30 is positioned to secure a base in position upon the pedestals with opposed peripheral portions of the base clamped between the upper surfaces of the pedestals and the clamping element.

A set of pin engaging members 32 is adapted to be positioned atop the platform 17. Each pin engaging member includes a cylindrical support 33 having an engaging pin 34 extending upwardly from one face thereof. The supports 33 are adapted to be positioned upon the platform 17 with the engaging pins 34 extending upwardly at right angles relative to the platform 17. Upon being positioned on the platform 17, the supports 33 can be slid or moved across the platform such that the engaging pins 34 are aligned for insertion into the holes of a dental base secured atop the pedestals 12. Preferably, the supports 33 and platform 17 are magnetically attracted to each other such that the pin engaging members 32 are maintained by the magnetism in their aligned positions upon the platform 17. In a preferred embodiment, the platform 17 is constructed of ferrous material such as stainless steel and the supports 33 are magnetized. Conversely, the supports could be ferrous and the platform magnetized or both platform and supports magnetized to achieve the same result. A magnetic strip 36 is provided adjacent the platform 17 to receive and hold pin engaging members that are not in use as illustrated in FIG. 1.

Figure 4:
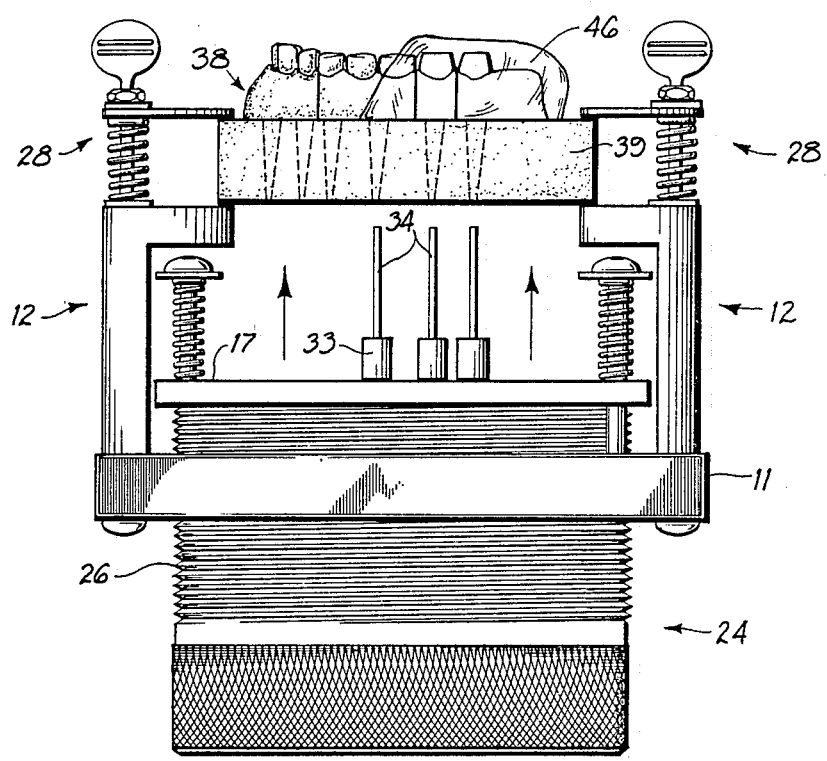
FIG. 4 is a side elevational view of the apparatus of FIG. 1 showing a base bearing a waxed dental cast secured to the apparatus for separation of the working dies of the cast from the base.

Referring to FIG. 4, it can be seen that the engaging pins are preferably the same length such that the upper ends of the engaging pins lie in a plane parallel to the platform 17 and parallel to the base bottom. The engaging pins therefore tend to engage the ends of the dowel pins simultaneously upon movement of the platform toward the base to dislodge each working die of the cast simultaneously from the base.

OPERATION

Figure 3:
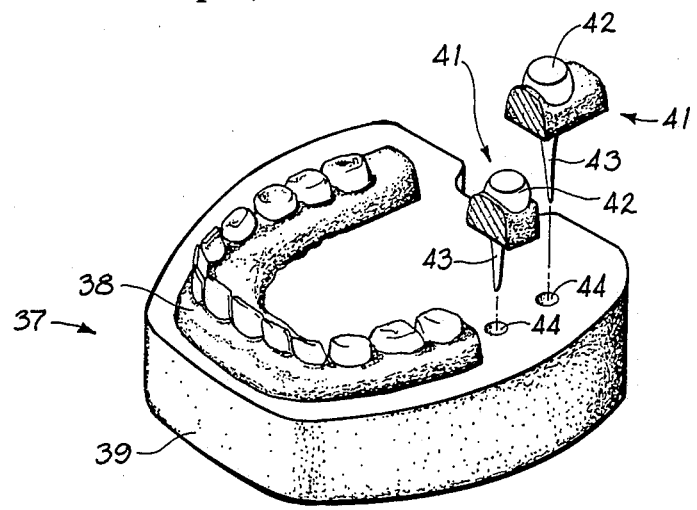
FIG. 3 is a perspective view of a typical dental model showing the individual working dies of the dental cast secured to the base with parallel tapered dowel pins.

FIG. 3 shows a typical dental model 37 for use in fabricating, bridges, splints and the like with the model comprising a cast 38 of a patient's teeth mounted atop a plaster base 39. Portions of the cast corresponding to teeth that have been prepared by the dentist to receive the bridge are cut by a dental technician into individual segments or dies 41 each bearing a prepared tooth 42. A tapered metal dowel pin 43 is embedded in each die and extends downwardly therefrom. A set of corresponding holes 44 extend through the base 39 with the holes positioned to receive the pins 43 such that the dies 41 are mounted to the base 39 with the pins 43 secured within the holes 44. When secured to the base in this way, the dies 41 align to define the cast that represents a patient's mouth as seen in FIG. 4.

The process of forming the dental cast 38 from a dentist's impression, embedding the dowel pins 43 therein, mounting the cast atop a wet plaster base with the pins extending through the base and cutting the cast into individual segments 41 is a common procedure in dental technology and well understood by those of skill in the art. The pins 43 are usually embedded within the cast 38, for example, using a parallel pin drill press such as a Pindex system.

Preferably, in preparing a dental model for use with the present invention, the dowel pins 43 are sized to extend slightly beyond the lower surface of the base 39 when the cast is embedded in the base and, when the plaster base dries, the lower surface is sanded flat such that the dowel pin ends are flush with the flattened base lower surface as seen in FIG. 4. The base bottom is then checked to make sure that it is indeed flat by, for example, placing it on a flat surface and insuring that it does wobble. The sanding of the base bottom and pins to form a flat surface with flush pins ends is not a common step with prior art methods. It is, however, an important first step in the present invention because it insures that the dowel pin ends lie in the plane of the base bottom which is turn is supported upon the pedestals in parallel relationship relative to the ends of the engaging pins. In this way, the engaging pins positioned platform on the always engage the ends of the dowel pins simultaneously.

With the dental model thusly prepared, the working dies of the cast which are to receive the bridge are coated with wax 46 (FIG. 4) that will ultimately become the dental pattern used by the dental technician to cast the dental bridge. The waxed model is then positioned upon the upper surfaces 14 of the pedestals 12 and secured thereon with clamps 28. The pin engaging members 32 are placed upon the platform beneath the dental model and positioned to align the engaging pins 34 for insertion into the holes 44 of the base upon movement of the platform 17 toward the base.

With the dental model and engaging pins in position, the driver 24 is rotated to advance it through the frame member 11 and to engage the upper surface 27 of the driver with the bottom of the platform 17. Further rotation of the driver moves the platform upwardly toward the base 39 as indicated by the arrows in FIG. 4. As the platform 17 moves upwardly, the engaging pins 34 simultaneously engage the ends of the dowel pins 43 with further upward movement of the platform 17 dislodging the dowel pins 43 to separate the waxed dental cast dies 41 from the base 39 and move them upwardly away from the base at the same rate.

Since the working dies are dislodged and separated from the base simultaneously, the dies maintain their relative position and the wax pattern 46 does not become deformed or warped as commonly occurs when the pins 43 were manually pressed from the base by a dental technician in the heretofore common manner. Even small differences in separations of the working dies can result in deformities of the wax pattern that can only be detected after the completed bridge has been cast from the wax pattern. Many times, the only solution to such a problem has been to scrap the bridge and start over or to repair the deformed bridge by cutting and soldering it sacrificing many hours of effort. With the present invention, however, the working dies of the dental cast are always dislodged and separated simultaneously from the base such that a dental technician can be confident that a bridge formed from the resulting wax pattern will fit the cast made from the dentist's impression.

The invention has been described in terms of a preferred embodiment. It will be obvious to those of skill in the art, however, that many modifications, additions and deletions could be made to the described embodiment. The invention might, for example, be used with equal advantage in forming dental prosthesis other than bridges or splints such as simi or precision attachments or implants. Further, other configurations of the platform such as round or disk shaped and various methods of mounting and securing the base in spaced relationship relative to the platform could be substituted for the pedestals and clamps of the preferred embodiment. Finally, the preferred embodiment has been described with the dental model secured and the platform movable toward it. It will be obvious that the platform could be secured and the dental model moved toward the platform if desired to achieve the same results. These and other modifications might be made to the preferred embodiment without departing from the spirit and scope of the invention as set forth in the claims.

What is claimed is:

1. An apparatus for simultaneously separating segments of a dental cast from their plaster base wherein the segments are mounted to the base with pins positioned within holes that extend through the base, said apparatus comprising:
   a platform;
   mounting means for mounting, the base in a predetermined position spaced from said platform;
   pin engaging means adapted to be positioned upon said platform and aligned for insertion into the holes of a base located at said predetermined position; and
   means for moving said predetermined position and said platform toward each other,
   whereby the pin engaging means engages the dental cast pins upon relative movement of the platform and base to dislodge the pins and separate the dental cast segment from the base.

2. The apparatus of claim 1 wherein said pin engaging means comprises a set of supports constructed to rest and slide upon said platform with each support having an engaging pin extending upwardly therefrom toward said predetermined position when said support is resting upon said platform.

3. The apparatus of claim 2 wherein said engaging pins are sized to engage the dental cast pins simultaneously upon movement of said platform and a base located at said predetermined position toward each other.

4. The apparatus of claim 2 wherein said supports are magnetically attracted to said platform.

5. The apparatus of claim 1 wherein said means for moving said predetermined position and said platform toward each other comprises a frame member positioned beneath said platform and bearing threaded driver means adapted to be advanced through said frame member into engagement with said platform to urge the platform toward the predetermined position.

6. The apparatus of claim 1 further comprising a frame member positioned beneath said platform and wherein said mounting means comprises at least two pedestals extending upwardly from said frame member with said pedestals having upper surfaces adapted to receive and support peripheral portions of a dental model base.

7. The apparatus of claim 6 further comprising clamp means for securing the base peripheral portions in position upon said pedestal upper surfaces.

8. An apparatus for simultaneously separating segments of a dental cast from their plaster base wherein the segments are mounted to the base with pins positioned within holes that extend through the base, said apparatus comprising:
   a substantially rectangular platform having an upper surface and a lower surface;
   a frame member positioned beneath said platform;
   means for supporting the base in a predetermined position spaced from said platform with said means comprising a pair of pedestals extending upwardly from said frame member adjacent opposed legs of said platform with each of said pedestals bearing an upper surface adapted to receive and support a peripheral portion of the base;
   clamp means for securing peripheral portions of the base in position upon said pedestals;
   means for moving said platform toward a base located at said predetermined position comprising a driver member adapted to be advanced through said frame member to engage the lower surface of said platform and urge the platform toward said predetermined position; and
   a set of engaging pins adapted to be positioned upon said platform and aligned for insertion into holes of a base located at said predetermined position to engage the pins therein upon movement of said platform toward the base,
   whereby the engaging pins engage the dental cast pins upon movement of the platform toward the base to dislodge the dental cast pins and separate the segments from the base.

9. The apparatus of claim 8 wherein the engaging pins are sized to engage the dental cast pins simultaneously upon movement of said platform toward the base.

10. The apparatus of claim 9 wherein said engaging pins extend upwardly from supports and wherein said supports are magnetically attracted to said platform.

11. A method of forming a pattern of a dental cast for use in fabrication of dental bridges and the like wherein segments of the dental cast are mounted to a plaster base with pins positioned within holes that extend through the base, said method comprising the steps of:
   (a) covering the dental cast segments with pattern forming material;
   (b) providing a platform;
   (c) mounting the base in a predetermined position spaced from the platform;
   (d) positioning pin engaging means upon the platform aligned for insertion into the base holes;
   (e) moving the platform and base toward each other to engage the pin engaging means and the pins;
   (f) further moving the platform and base toward each other to dislodge the pins from the holes and separate the dental cast segments from the base; and
   (g) removing the dental cast segments from the pattern forming material.

12. The method of claim 11 wherein the pin engaging means are sized to engage the pins simultaneously.

13. A pattern for use in fabricating dental bridges and the like with said pattern being formed by the method of claim 11.

* * * * *